United States Patent [19]

Rosenbluth et al.

[11] Patent Number: 4,958,630
[45] Date of Patent: Sep. 25, 1990

[54] METHOD AND APPARATUS FOR TREATING IMPOTENCE

[75] Inventors: Robert F. Rosenbluth, Laguna Niguel; Brian J. Cox, Lake Forest, both of Calif.

[73] Assignee: Advanced Surgical Intervention, Inc.

[21] Appl. No.: 418,286

[22] Filed: Oct. 6, 1989

[51] Int. Cl.⁵ .............................................. A61F 2/26
[52] U.S. Cl. ..................................................... 128/79
[58] Field of Search .............. 128/79, DIG. 25; 604/9

[56] References Cited

U.S. PATENT DOCUMENTS

| | | | |
|---|---|---|---|
| 3,750,194 | 8/1973 | Summers | 3/1 |
| 4,419,985 | 12/1983 | Trick | 128/1 |
| 4,424,807 | 1/1984 | Evan, Sr. | 128/79 |
| 4,428,365 | 1/1984 | Hakky | 128/1 |
| 4,572,168 | 2/1986 | Fischell | 128/79 |
| 4,596,242 | 6/1986 | Fischell | 128/79 |
| 4,604,994 | 8/1986 | Sealfon | 128/79 |
| 4,723,538 | 2/1988 | Stewart et al. | 128/79 |
| 4,828,544 | 5/1989 | Lane et al. | 251/342 |
| 4,829,990 | 5/1989 | Thuroff et al. | 128/327 |

Primary Examiner—Cary E. Stone
Attorney, Agent, or Firm—Klein & Szekeres

[57] ABSTRACT

A method for the treatment of impotence in a human male patient includes the steps of (1) selecting a penile vein or a crus of a corpus cavernosum; and (2) implanting in the patient a vascular occlusion device that allows the selective restriction of the flow of blood from the selected vein or crus when erectile function is desired, normal flow being otherwise maintained. A preferred embodiment of the vascular occlusion device comprises an inflatable cuff adapted to receive the vein or crus, a squeeze-bulb reservoir containing a working fluid, and a valving mechanism that allows fluid to flow from the squeeze bulb to the cuff, through a tube, when the bulb is squeezed, thereby inflating the cuff to restrict blood flow through the vein or crus. To deflate the cuff, the valving mechanism is manually operable to allow fluid to flow out of the cuff back into the reservoir due to the pressure gradient created by the partial evacuation of the previously-squeezed bulb. A drainage channel is provided in the valving mechanism to provide automatic and gradual cuff deflation over a selected time interval. Alternative embodiments of the invention include the surgical creation of an arteriovenous anastamosis that is received in a second cuff operated in a complementary manner with the first cuff, and the provision of a drug delivery adaptor that delivers a measured dose of a drug to the penile tissue in response to the squeezing of the bulb.

29 Claims, 2 Drawing Sheets

METHOD AND APPARATUS FOR TREATING IMPOTENCE

BACKGROUND OF THE INVENTION

The present invention relates generally to the field of treatments for male erectile impotence. More specifically, it relates to a method and apparatus for treating impotence by controlling vascular blood flow through the penis.

Efforts to treat male erectile impotence have, in recent years, largely focused on implantable, inflatable prosthetic devices, such as those described in U.S. Pat. Nos. 4,596,242 and 4,572,168, both to Fischell. Typically, such prosthetic devices comprise an inflatable chamber surgically implanted within the penis, and a manual pump for controllably inflating the chamber with a biocompatible working fluid that is stored in a reservoir. Both the pump and the reservoir may also be surgically implanted, the pump being located in a portion of the anatomy (e.g., the scrotum) that permits convenient manual operation.

While such inflatable prostheses have achieved relatively widespread use, they do have some drawbacks. For example, the surgery required to implant these devices necessitates substantial and irreversible trauma to the internal tissues of the penis, leading to life-long dependency on the prosthesis. Similarly, repair and replacement of the prosthesis also require major surgery. The need to inflate the prosthesis necessitates a relatively large fluid reservoir that also must be surgically implanted, and which may cause discomfort to the user. The relatively large volume of working fluid often requires a considerable amount of pumping by the user to achieve erection, and the erection achieved may often be less than totally natural, in terms of size, rigidity, firmness, and angle.

While many patients have benefited from the inflatable implants described above, the limitations inherent in such devices have lead to the exploration for alternative therapies. Some success in this regard has been achieved for patients who suffer from certain types of vascular dysfunction in the venous system of the penis. Such patients experience venous incompetence, manifesting itself in abnormal venous drainage from the corpora cavernosa, the penile chambers that are normally distended with blood to achieve erection.

It has long been recognized that such venous incompetence can be treated by occluding one or more major penile veins, such as the deep dorsal vein. Venous occlusion is typically performed by ligation and/or balloon embolization. See, e.g., Lewis, "Venous Surgery for Impotence", *Urologic Clinics of North America*. Vol. 15, No. 1, Feb., 1988; Orvis et al., "New Therapy for Impotence", *Urologic Clinics of North America*, Vol. 14, No. 3, Aug., 1987; Trieber et al., "Venous Surgery in Erectile Dysfunction: A Critical Report on 116 Patients", *Urology*, Vol. 34, No. 1, July, 1989. Encouraging success rates have been achieved in suitable candidates for such surgery, with many patients being able to achieve substantially natural erections. Furthermore, the surgical procedures involved, while delicate, result in relatively little trauma to the penile tissue, leaving the tissue substantially intact except for the particular blood vessels involved in the surgery. Moreover, by leaving the corpora cavernosa and penile nerves virtually intact, the vascular occlusion technique is suitable for use in conjunction with pharmacological therapies.

With surgical vascular occlusion, however, relief is temporary in many cases, with collateralization of the penile veins being suspected as a principal cause of eventual failure. Such collateralization is considered to be a natural consequence of the permanent occlusion of a major venous path.

Consequently, there is a need for a treatment for impotence that provides all of the benefits of venous occlusion surgery, and yet which is less susceptible to long-term failure.

SUMMARY OF THE INVENTION

Broadly, the present invention is a method and apparatus for treating impotence that provides selective, intermittent, and reversible occlusion of one or more of the penile blood vessels, the occlusion being controllably provided only when an erection is desired.

More specifically, in accordance with a preferred embodiment of the invention, an inflatable cuff is surgically wrapped around a major penile vein or a portion of one of the corpora cavernosa. The cuff is selectably and controllably inflated by working fluid delivered from a squeeze-bulb reservoir implanted in the patient's scrotum, the fluid being delivered through a valving mechanism attached to the squeeze-bulb and implanted with it.

When an erection is desired, the squeeze-bulb is palpated, causing the fluid to flow through the valving mechanism into the cuff, thereby inflating the cuff to occlude or partially occlude the vein or veins engaged by the cuff. The degree of occlusion so obtained should enhance venous competence sufficiently to provide an essentially natural erection in many patients.

To achieve detumescence, the valving mechanism can be manually opened to allow the backflow of fluid from the cuff into the squeeze-bulb, thereby reopening the vein or veins and allowing the drainage of blood from the corpora cavernosa. The valving mechanism is preferably provided with a narrow drainage passage that allows a slow backflow back into the squeeze-bulb from the cuff. The diameter of the drainage passage is calculated to allow the cuff to deflate gradually over an interval of about 20 to 30 minutes, in the event that the user neglects to open the valving mechanism manually.

The present invention offers all of the advantages of conventional venous occlusion surgery, with several further advantages. For example, the erectile structures of the penis are left completely intact, so that the surgery is reversible. Venous drainage is allowed at all times that the cuff is not inflated, and the intermittent venous occlusion provided by the invention is under the control of the user. Most importantly, it is expected that with venous occlusion occurring only intermittently, the probability of venous collateralization will be significantly reduced, or, alternatively the amount of time that elapses before collateralization occurs will be substantially increased.

Another advantage of the present invention is its susceptibility to a number of variations on the general theme. One variation, already alluded to, is that, rather than wrapping the cuff around a discrete vein, the cuff may be wrapped around a portion of a corpus cavernosum, thereby effectively cuffing a bundle of veins. Similarly, two or more discrete veins can be cuffed.

Another variation is that a shunt may be surgically provided between the cuffed vein and a nearby artery with a second inflatable cuff being wrapped around the shunt. In this two-cuff embodiment, the valving mechanism is modified so that the shunt cuff is normally inflated while the venous cuff is normally deflated. When an erection is desired, the venous cuff is inflated to occlude the vein while the shunt cuff is simultaneously deflated to open the shunt. This manner of operation results in a partial arterialization of venous drainage to improve erectile function in those patients with an arterial insufficiency. As an option, the anastomosis may be left uncuffed, thereby maintaining a continuous arterialization of the venous tree.

In still another variation, the pressure of the working fluid used to inflate the cuff or cuffs is also used to pump a vasoactive drug into the penile tissue from a second implanted reservoir. In this embodiment, the invention functions as both a venous occlusion device and a drug delivery device.

It will thus be appreciated that the present invention offers a number of significant advantages over prior methods and devices for the vascular treatment of impotence. These and other advantages will be more fully understood from the detailed description that follows.

DETAILED DESCRIPTION OF THE INVENTION

Referring now to the drawings, FIGS. 1 through 7 and 12 through 14 illustrate a preferred embodiment of the apparatus of the present invention.

As shown in FIGS. 1 through 7, the apparatus is a vascular occlusion device 10, comprising an inflatable cuff 12 connected by a cuff inflation tube 14 to a squeeze-bulb reservoir 16 through a valving mechanism 18. The cuff 12 is an open-ended, hollow cylinder of polyurethane, silicone rubber, or another suitable biocompatible material. The cuff 12 is axially divided to form a longitudinal gap 20, on either side of which is provided a suture tab 22. The gap 20 communicates with an axial bore 24 through the cuff 12. The hollow interior of the cuff 12 defines an inflatable chamber 26, which communicates with the downstream end of the tube 14. The upstream end of the tube 14 communicates with the downstream end of the valving mechanism 18, the upstream end of which is in fluid communication with the squeeze-bulb reservoir 16.

Figures 8, 9, 10, 11, 12:
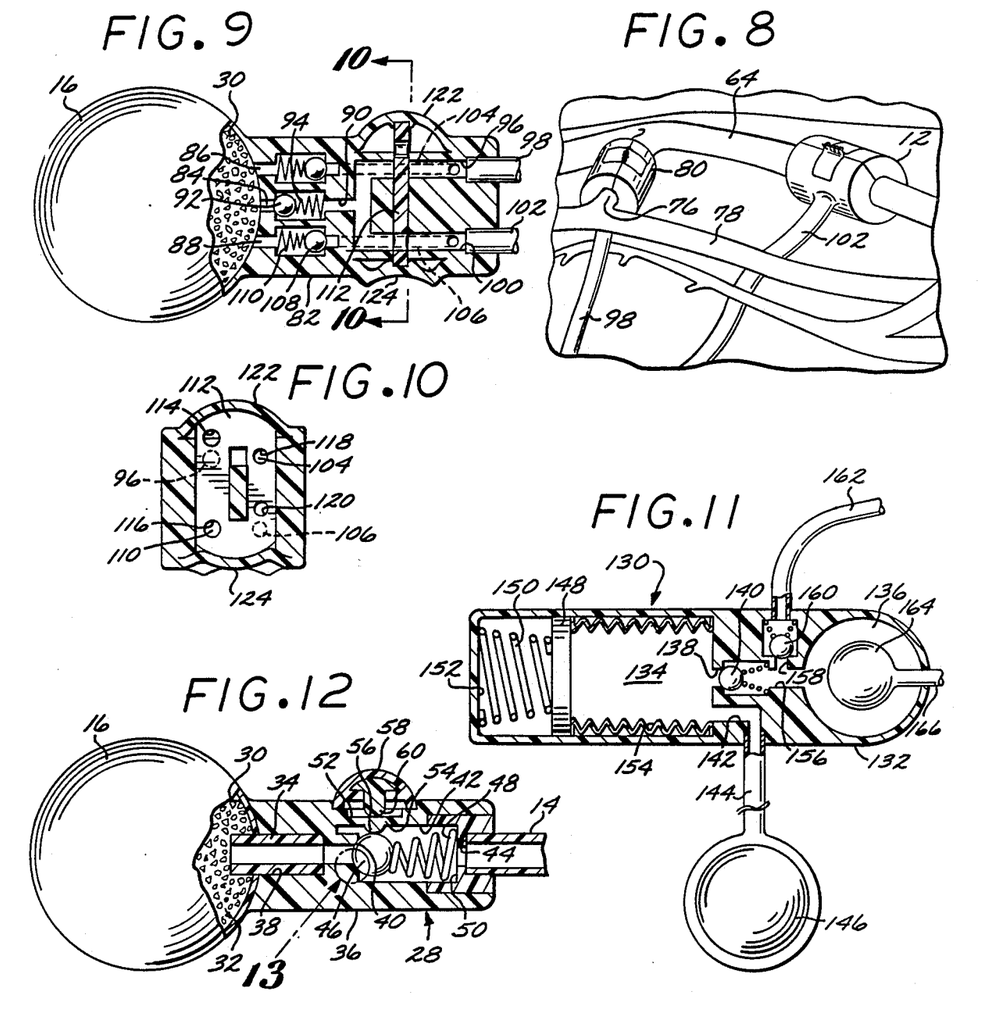
FIG. 8 is a detailed perspective view of the implanted cuffs of an embodiment of the invention in which both a vein and an anastamosis are cuffed.
FIG. 9 is a cross-sectional view of a valving mechanism used with the two-cuff embodiment of FIG. 8.
FIG. 10 is a cross-sectional view along line 10—10 of FIG. 9.
FIG. 11 is a cross-sectional view of an implantable drug delivery adaptor that may be used with the apparatus of the present invention.
FIG. 12 is a cross-sectional view of a valving mechanism used in the preferred embodiment of the invention shown in FIGS. 1 through 7.
Figure 13:
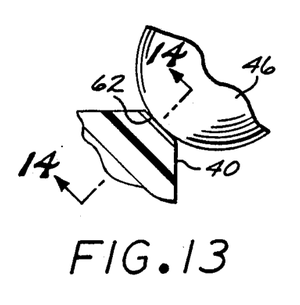
FIG. 13 is a detailed view of the valve structure shown within the dashed circle 13 of FIG. 12.
Figure 14:
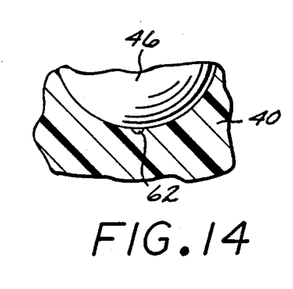
FIG. 14 is a cross-sectional view taken along line 14—14 of FIG. 13.

FIGS. 12, 13, and 14 illustrate an integral reservoir and valving mechanism assembly 28, in accordance with a preferred embodiment of the apparatus of the invention. The reservoir 16 comprises a hollow, substantially spherical shell 30 formed from polyurethane, or another flexible biocompatible material. The interior of the shell 30 is filled with an open-celled elastomeric foam material 32, the interstices of which are filled with a biocompatible working fluid, preferably with radiographic contrast capability. A fluid flow conduit 34 extends from the interior of the reservoir outwardly through the shell 30.

The shell 30 is bonded to the upstream end of a valve housing 36, the latter having a receptacle 38 dimensioned to receive the fluid flow conduit 34 with a snug, fluid-tight fit. The housing 36, which may be made of any suitable biocompatible polymer, defines a fluid flow passage, the upstream end of which is defined by the fluid flow conduit 34 received in the receptacle 38. The passage extends downstream from the fluid flow conduit 34, through a valve seat 40, a valve chamber 42, and finally through an outlet 44 that is fluidly connected to the upstream end of the lumen 14. The valve chamber 42 contains a check valve, comprising a ball 46 that is biased against the valve seat 40 by a coil spring 48. The spring 48, in turn, is captured between the ball 46 and a shoulder 50 that forms the downstream wall of the chamber 42.

A circular recess 52 is formed in the outer wall of the housing 36, thereby defining a thin-walled portion 54 that is resiliently flexible. The interior surface of the thin-walled portion 54 is provided with a protuberance 56 that abuts against the ball 46. A push-button 58 is captured in the recess 52, and has a protuberance 60 that engages the outer surface of the thin-walled portion 54. Depression of the push-button 58 flexes the thin-walled portion 54, thereby pushing the ball 46 away from the valve seat 40 to open the valve defined by the ball 46 and the valve seat 40, permitting fluid to flow through the fluid flow passage. Releasing the push-button 58 allows the spring 48 to return the ball 46 to its closed position against the valve seat 40.

As shown in FIGS. 13 and 14, the valve seat 40 is provided with a narrow, restricted drainage channel 62 that remains open when the ball 46 is seated against the valve seat 40. This drainage channel 62 provides a backflow passage from the downstream side of the valve to the upstream side of the valve when the valve is closed, for purposes to be described below.

The structure of the preferred embodiment of FIGS. 1 through 7 and 12 through 14 having now been described, its function and method of use can now be easily understood.

Figures 1, 2, 3, 4, 5, 6, 7:
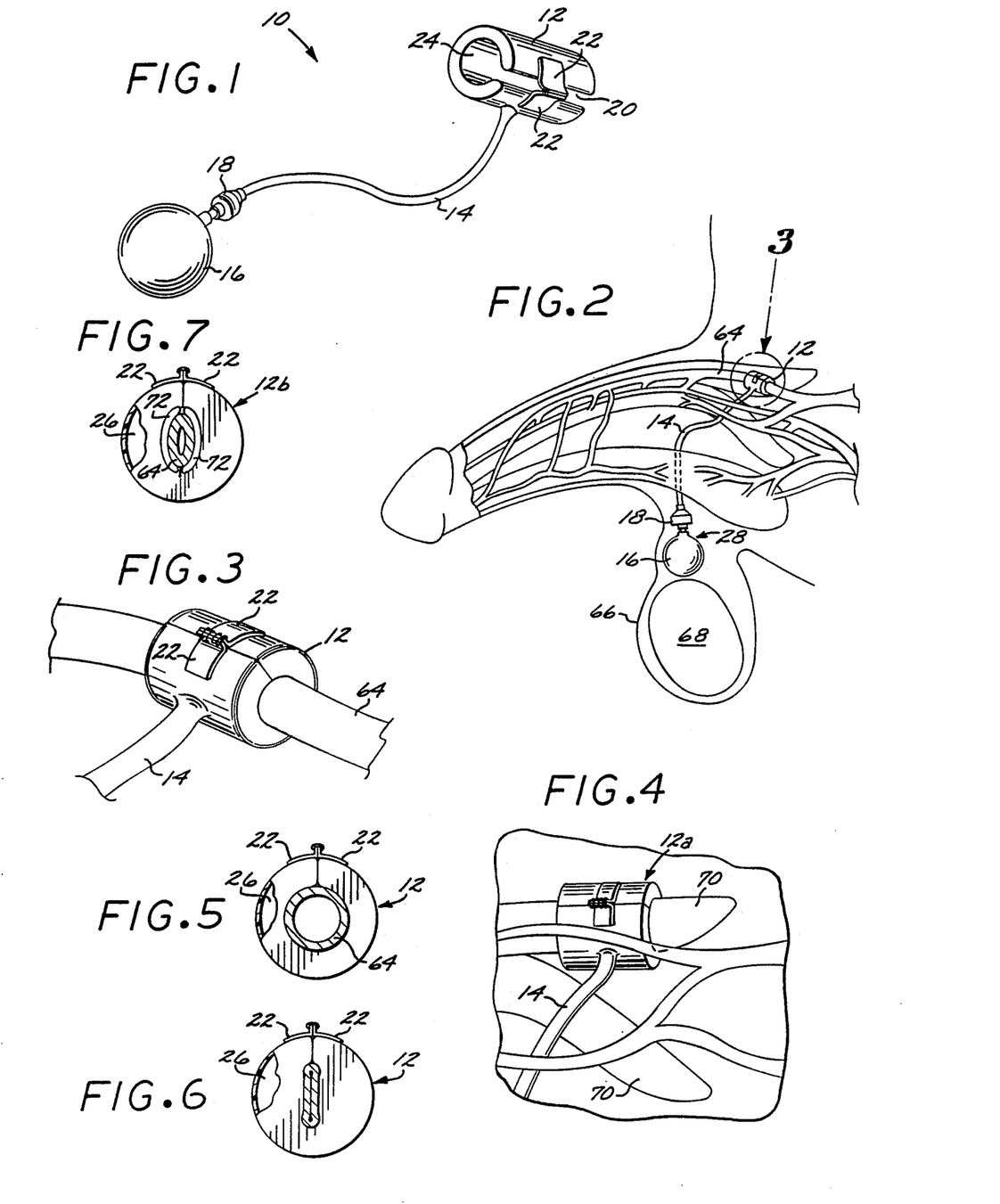
FIG. 1 is a perspective view of an apparatus for treating impotence in accordance with a preferred embodiment of the present invention.
FIG. 2 is a simplified cross-sectional view of a human male's genitalia, showing the apparatus of FIG. 1 implanted therein.
FIG. 3 is a detailed perspective view of the cuff shown within the dashed circle 3 of FIG. 2.
FIG. 4 is a view similar to that of FIG. 3, but showing the cuff wrapped around the crus of a corpus cavernosum.
FIG. 5 is an end view of the cuff of FIG. 3, partially broken away, showing a vein within the cuff in cross-section, the cuff being in a deflated state.
FIG. 6 is a view similar to that of FIG. 5, showing the cuff in an inflated state.
FIG. 7 is an end view of a modified cuff in the inflated state.

Implantation of the vascular occlusion device 10 is begun by surgically exposing a major penile vein, such as the deep dorsal vein, indicated in FIG. 2 by the numeral 64. Other major veins, such as the pudendal vein or the cavernous vein, may be selected. (As used herein, the term "penile vein" means any vein that drains the penis.) The surgical techniques for exposing these veins are well-known, and need not be described herein. The cuff 12 is then wrapped around the selected exposed vein and secured in place by suturing the suture tabs 22. While the use of suture tabs is preferred, other means for securing the cuff, such as snap fasteners or hook-and-loop fasteners, may be employed.

The cuff inflation tube 14 is then routed downwardly through the surrounding tissue to place the reservoir and valving mechanism assembly 28 in the upper part of the scrotum (designated in FIG. 2 by the numeral 66), just above the testes 68. The assembly 28 should be oriented so that the push-button 58 (FIG. 12 lies just below the skin, where it can be manually operated by the patient. In some patients, it may be desirable to route the tube 14 upwardly into the abdomen to place the reservoir and valving mechanism assembly just below the skin in the groin area. Nevertheless, the scrotal location makes palpation of the squeeze-bulb reservoir 16 much easier, and operation of the push-button 58 more convenient, for most patients.

FIG. 4 shows an alternative implantation site for a modified cuff 12a wherein at least one crus 70 of one of the corpora cavernosa is wrapped by a cuff 12a. This site offers the advantage of occluding a bundle of veins (not shown) that extend through the crus 70. The cuff 12a used for this site would be somewhat larger than the cuff 12 used to occlude only a single discrete vein. As still another alternative, two or more discrete veins may be cuffed, each with a single cuff connected by a tube to a common reservoir and valving mechanism assembly. In such multi-cuff applications, the reservoir might advantageously have a greater volume than that employed in single cuff applications.

The implanted vascular occlusion device 10 operates as follows: When the patient desires to achieve an erection, he manually palpates the reservoir 16, thereby squeezing the working fluid through the conduit 34 and the valve seat 40, past the ball 46 (which is pushed away from the seat by the fluid to open the valve), and finally through the chamber 42 and the outlet 44. The fluid then flows through the tube 14 into the interior of the cuff 12, which is thereby inflated.

The inflation of the cuff is illustrated in FIGS. 5, 6 and 7. FIG. 5 shows the cuff 12 in its uninflated state, with the vein 64 open. FIG. 6 shows the vein 64 occluded by the cuff 12 in its inflated state. The cuff 12a of FIG. 4 would similarly occlude a plurality of veins within the cuffed crus 70.

In some cases, it may be desirable and sufficient to provide only a partial occlusion, or restriction, of the selected vein 64. In such cases a modified cuff 12b is used, as shown in FIG. 7. In the modified cuff 12b, the axial bore is lined with a pair of curved plates 72 in diametric opposition. When the cuff is inflated, the plates 72 engage each other to prevent a total occlusion of the vein.

With the cuff inflated, venous outflow through the occluded vein or veins is severely restricted, thereby improving the degree of tumescence of the penis to provided an enhancement of the patient's erectile function.

When detumescence is desired, the patient pushes the push-button 58 to urge the ball 46 off of the valve seat 40, thereby opening the valve. The squeeze-bulb reservoir 16, having been evacuated by palpation, as described above, presents a low-pressure area that draws the working fluid from the cuff 12, through the tube 14, and back through the valve mechanism and into the reservoir 16. As a result, the cuff is collapsed, thereby re-opening the previously-occluded vein or veins to allow the outflow of blood, with resulting detumescence.

The drainage channel 62 provides a gradual deflation of the cuff in the event that the patient neglects to operate the push-button 58. The channel 62 has a diameter that is calibrated to to allow a backflow into the reservoir 16 at a pre-determined rate, thereby causing the cuff to become deflated after a pre-determined interval. The interval may be selected, for example, to achieve detumescence after about 20 to 30 minutes, or longer.

FIGS. 8, 9, and 10 illustrate a modification of the invention, in which an arterializing shunt, or anastamosis 76 is surgically created between the cuffed vein 64 and a nearby artery 78, as shown in FIG. 8. The anastamosis 76 diverts some of the arterial inflow back into the venous tree upstream from the cuff 12, thereby improving erectile function in those patients having an arterial insufficiency. It may be advantageous to use an optional second cuff 80 on the anastamosis 76. The second cuff 80 is preferably operated so that it remains inflated to close or restrict the anastamosis 76 when the venous cuff 12 is open. This "detumescent" mode maintains the patient's normal blood circulation pattern when an erection is not desired. When an erection is desired, on the other hand, a "tumescent" mode is entered, in which the venous cuff 12 is inflated, and the anastamosis cuff 80 is deflated. Thus, the vein 64 is occluded or partially occluded, and the anastamosis 76 is opened, to provide the desired reduction in blood outflow and increase in blood inflow. By cuffing the anastamosis 76, it is used only when needed, so as to maintain normal vascularization to the maximum extent possible. It will be appreciated that the anastamosis 76, and its associated cuff 80, can be used with the crus cuff 12a, shown in FIG. 4.

Cuffing of the anastamosis 76 requires a modification of the valving mechanism for inflating and deflating the venous cuff 12 and the anastamosis cuff 80. Such a modified valving mechanism is shown in FIGS. 9 and 10. The modified mechanism includes a valve housing 82, the upstream end of which is bonded to the shell 30 of the squeeze-bulb reservoir 16. The housing has an inlet 84, a first backflow outlet 86, and a second backflow outlet 88, all communicating with the interior of the reservoir 16. The inlet 84 communicates with a flow channel 90 through an inlet check valve, which may comprise a ball 92 biased against a valve seat by a spring 94. The flow channel 90 branches into a first outflow branch 96 which communicates, via a first cuff inflation tube 98, with the anastamosis cuff 80, and a second outflow branch 100 which communicates, via a second cuff inflation tube 102, with the venous cuff 12.

The first backflow outlet 86 communicates with a first backflow passage 104 through a first backflow check valve and the second backflow outlet 88 communicates with a second backflow passage 106 through a second backflow check valve. Each of the backflow check valves may comprise a ball 108 biased against a valve seat by a spring 110. The backflow passages 104 and 106 are laterally offset from the first and second outflow branches 96 and 100, respectively, and open into the first and second outflow branches, respectively, downstream from a slide member 112.

The slide member 112 is slidably disposed transversely in the valve housing 82 so as to intersect the first and second outflow branches 96 and 100, and the first and second backflow passages 104 and 106. One side of the slide member 112 has a first pair of vertically-aligned (as oriented in the drawings) holes 114 and 116, while the other side of the slide member 112 (as viewed in FIG. 10) has a second pair of vertically-aligned holes 118 and 120. The slide member 112 is movable between a first position (shown in FIGS. 9 and 10), and a second position (not shown). In the first position, the lower hole 116 of the first pair of holes is aligned with the second outflow branch 100, and the upper hole 114 of the first pair of holes is out of alignment with the first outflow branch 96. Conversely, with second pair of holes, the lower hole 120 is out of alignment with the second backflow passage 106, and the upper hole 118 is aligned with the first backflow passage 104. When the slide member 112 is moved to the second position (not shown), this arrangement of hole and passage alignment is reversed: the lower hole 116 of the first pair is out of alignment with the second outflow branch 100; the upper hole 114 of the first pair is aligned with the first outflow branch 96; the lower hole 120 of the second pair is aligned with the second backflow passage 106; and the upper hole 118 of the second pair is out of alignment with the first backflow passage 104.

Thus, with the slide member 112 in the first position, the first outflow branch 96 and the second backflow passage 106 are closed; the second outflow branch 100 and the first backflow passage 104 are open. Palpation of the squeeze bulb 16 will thus cause the working fluid to be pumped out of the anastamosis cuff 80, through the first cuff inflation tube 98, the first backflow passage 104, the first backflow check valve, and the first backflow outlet 86, into the squeeze bulb 16, from which the fluid then enters the inlet 84, passing through the inlet check valve, the flow channel 90, the second outflow branch 100, and the second cuff inflation tube 102 to inflate the venous cuff 12.

With the slide member in the second position, the first outflow branch 96 and the second backflow passage 106 are open; the second outlet branch 100 and the first backflow passage 104 are closed. Palpation of the squeeze bulb 16 will thus cause the working fluid to be pumped from the venous cuff 12 to the anastamosis cuff 12 via the second backflow passage 106, the second backflow check valve, the second backflow outlet 88, the inlet 84, the inlet check valve, the flow channel 90, and the first outflow branch 96.

Movement of the slide member 112 between the first and second positions is effected by a pair of opposed push-buttons 122, 124 that operatively engage opposite ends of the slide member 112.

Thus, by means of the push-buttons 122, 124, the patient can select a detumescent mode, in which the anastamosis cuff 80 is inflated to close or restrict the anastamosis 76, while the venous cuff 12 is deflated to maintain normal venous outflow. When an erection is desired, the push-buttons are manipulated to select a tumescent mode, in which the venous cuff 12 is inflated to occlude or restrict venous outflow, while the anastamosis cuff 80 is deflated to open the anastamosis 76, thereby arterializing the venous outflow.

FIG. 11 illustrates a further modification of the invention, in the form of a drug delivery adaptor 130, which may advantageously be added for those patients who would benefit from a vasoactive drug, such as papaverine.

The adaptor 130 comprises an implantable housing 132 of a suitable biocompatible polymer. The housing contains a first reservoir 134 at one end, and a second reservoir 136 at the other end. The first reservoir 134 has an outlet 138 that is normally closed by a first check valve 140, preferably a spring-loaded ball, as shown. An inlet 142 to the first reservoir is connected by a tube 144 to an implantable injection port 146, of a type well-known in the art. Means are provided for varying the volume of the first reservoir 134, preferably comprising a piston 148 biased by a spring 150 seated against an interior wall 152 of the housing 132. The first reservoir 134 is advantageously lined with a collapsible bellows 154 to minimize leakage around the piston 148.

The second reservoir 136 has an inlet 156 that communicates with the first reservoir outlet 138 by means of the first check valve 140. An outlet 158 from the second reservoir 136 communicates, via a second check valve 160, with one end of a drug delivery tube 162, the other end of which (not shown) is located at the desired site within the penile tissue for delivery of the vasoactive drug. The second check valve 160, like the first check valve 140, is preferably a spring-loaded ball but with a stiffer spring constant than the first check valve 140. The interior of the second reservoir 136 contains a balloon 164 that is inflatable through an inflation tube 166, which is connected to the cuff-inflation tube of the vascular occlusion device 10, described above.

In operation, the adaptor 130 is implanted into the patient's body at a convenient site. A vasoactive drug is injected into the injection port 146, from which the drug flows into the first reservoir 134. The first reservoir 134 expands, by means of the piston 148, to receive a sufficient supply of the drug for delivery of a multiplicity of doses before refilling is needed. During the filling process, the drug also flows into the second reservoir 136 through the first reservoir outlet 138, the first check valve 140, and the second reservoir inlet 156, thereby filling the second reservoir 136 (the balloon 164 being collapsed).

When it is desired to deliver a dose of the drug to the patient, the balloon 164 is inflated with working fluid delivered through the tube 166 by palpation of the squeeze bulb reservoir 16 of the vascular occlusion device 10. The inflation of the balloon 164 displaces the drug from the second reservoir 136, through the second reservoir outlet 158, the second check valve 160, and out to the penile tissue through the drug delivery tube 162. It will be appreciated that the volume of the second reservoir 136, with the balloon collapsed, is preferably calibrated so as to contain a single measured dose of the drug.

The balloon 164 is then collapsed or deflated by withdrawing the working fluid back into the squeeze-bulb reservoir 16 in the manner previously described (i.e., by operating the push-button 58 in the valving assembly illustrated in FIG. 11). The resultant evacuation of the second reservoir 136 causes another dose of the drug to be drawn from the first reservoir 134 into the second reservoir 136 through the first reservoir outlet 138, the first check valve 140, and the second reservoir inlet 156. The volume of the first reservoir is correspondingly contracted by the spring-biased piston 148. The drug delivery adaptor 130 is now ready for delivery of the next dose.

Use of the adaptor 130 may require a somewhat larger volume for the squeeze-bulb reservoir 16 than would otherwise be necessary, due to the need to inflate both the vascular occlusion cuff and the balloon 164.

The drug delivery adaptor 130 thus delivers the vasoactive drug in response to the same pressurized flow of working fluid inflates the vascular occlusion cuff 12 or 12a. As a result, the drug is delivered to the tissue automatically at about the same time as the vascular occlusion occurs, thereby achieving the maximum benefit possible from the combined therapies.

It will be appreciated that the drug delivery adaptor 130 can be used without a vascular occlusion cuff for patients who are to be treated only by pharmacological means. The necessary modifications to the adaptor 130 would readily suggest themselves to those of ordinary skill in the pertinent arts.

From the foregoing description, it can be appreciated that the present invention offers a number of significant advantages over prior art methods and apparatus for treating impotence in those patients whose problems stem principally from vascular insufficiency. As compared to inflatable prosthetic implants, for example, the present invention requires much less extensive surgical alteration of penile tissue. Also, a much smaller volume of working fluid is required, thereby substantially decreasing the size of the fluid reservoir that needs to be surgically implanted. Furthermore, as compared to such prior art implants, a more natural erection, in terms of size, firmness, rigidity, and angle, is more easily attained. As compared to prior art vascular occlusion techniques, the probability of collateralization is substantially reduced. In addition, the present invention offers a large number of options as to implantation sites and occlusion sites. Moreover there is the option of providing the delivery of a vasoactive agent automatically along with the vascular occlusion.

While a preferred embodiment of the invention has been described herein, along with a few modifications, it will be appreciated that other variations and modifications will suggest themselves to those skilled in the pertinent arts. For example, the cuff configurations described herein are exemplary only, and other types of inflatable cuffs may be found to be effective. Indeed, other means may be devised for selectively and reversibly occluding one or more major penile veins or a crus of a corpus cavernosum. For example, an inflatable balloon may be implanted adjacent to a selected crus, whereby inflation of the balloon would result in a pressurized impingement on the crus sufficient to restrict blood flow therethrough.

Similarly, a number of functional equivalents may be found for the specific valving mechanisms described herein for the vascular occlusion device. With regard to the method of the present invention, other sites for the vascular occlusion cuff may be found to be suitable, besides those specifically mentioned herein. Furthermore, it will be appreciated that the invention described herein can be used in conjunction with other surgical techniques, such as, for example, venous ligation or embolization.

These and other variations and modifications should be considered to be within the spirit and scope of the present invention, as defined in the claims which follow.

What is claimed is:

1. A method of treating impotence in a human male patient, comprising the steps of:
   (a) selecting a penile vein or a portion of a crus of a corpus cavernosum in the patient;
   (b) implanting, in the body of the patient, implantable means for allowing the patient selectively to restrict the venous outflow of blood from the selected vein or crus when erectile function is desired, normal venous outflow for the patient being otherwise maintained; and
   (c) introducing a vasoactive drug into the penile tissue of the patient when the venous outflow is restricted.

2. The method of claim 1, wherein the implantable means comprises:
   an inflatable cuff adapted to receive and engage the selected vein or crus;
   an implantable reservoir containing a biocompatible working fluid; and
   means for selectively inflating the cuff with the fluid from the reservoir when erectile function is desired.

3. The method of claim 1, wherein a penile vein is selected in the selecting step, and wherein the method further comprises the steps of:
   (d) selecting a penile artery near the selected vein; and
   (e) arterializing a portion of the venous blood flow by surgically creating an anastamosis between the selected vein and the selected artery.

4. The method of claim 1, wherein the implantable means comprises:
   an inflatable cuff adapted to receive and engage the selected vein or crus;
   an implantable reservoir containing a biocompatible working fluid;
   cuff inflation means for selectively inflating the cuff with fluid from the first reservoir when erectile function is desired;
   implantable chamber means for containing the vasoactive drug; and
   displacement means, operatively associated with the chamber means, for delivering a quantity of the vasoactive drug from the chamber means to the penile tissue of the patient.

5. A device for treating impotence in a human patient, comprising:
   an inflatable cuff, implantable in the patient so as to receive and engage a penile vein or a crus of a corpus cavernosum of the patient; and
   cuff actuation means, implantable in the patient, and operable by the patient, for selectively inflating and deflating the cuff, thereby selectively and reversibly restricting the blood flow through the vein or crus, the cuff actuation means comprising:
   a fluid-filled squeeze bulb;
   conduit means for providing fluid communication between the bulb and the cuff; and
   valving means for allowing the flow of fluid through the conduit means from the bulb to the cuff in response to the collapsing of the bulb due to the application of external pressure thereto, the valving means including a housing defining a fluid flow path between the bulb and the conduit means, and a valve element in the housing, movable between a first position in which the valve element is closed against a valve seat, thereby closing the fluid flow path, and a second position opening the fluid flow path, the valve element being movable from the first position to the second position in response to the pressure-induced collapsing of the bulb;

biasing means in the housing and engageable against the valve element, for biasing the valve element against the valve seat; and manual valve actuation means, operably associated with the valving means, for selectively moving the valve element from the first position to the second position in response to manual operation, thereby to allow the flow of fluid through the conduit means from the cuff to the bulb, the manual valve actuation means comprising:

means defining a flexible portion of the housing;

a push-button seated in the housing so as to be manually operable, the push-button including a protuberance that is engageable against the flexible portion; and valve element engagement means disposed on the flexible portion so as to be operably engageable against the valve element to displace the valve element from the valve seat in response to the flexing of the flexible portion when the push-button is operated to engage the protuberance against the flexible portion.

6. The device of claim 5, further comprising: automatic cuff deflation means for deflating the cuff when a predetermined time interval has elapsed.

7. The device of claim 6, wherein the automatic cuff deflation means comprises:

a drainage passage through the valve seat that remains open when the valve element is closed against the valve seat, the drainage passage having a diameter that is calculated to provide a rate of flow of fluid from the cuff to the bulb that results in the substantial deflation of the cuff when the predetermined time interval has elapsed.

8. The device of claim 5, further comprising: drug delivery means, implantable in the body of the patient, for delivering a predetermined quantity of a liquid to the penile tissue of the patient in response to the flow of fluid through the conduit means from the bulb to the cuff.

9. A device for treating impotence in a human male patient, comprising:

an inflatable cuff, implantable in the patient so as to receive and engage a penile vein or a crus of a corpus cavernosum of the patient; and cuff actuation means, implantable in the patient, and operable by the patient, for selectively inflating and deflating the cuff, thereby selectively and reversibly restricting the blood flow through the vein or crus, the cuff actuation means comprising:

a reservoir containing a fluid;

patient-operable pumping means for pumping the fluid from the reservoir into the cuff;

valving means, selectively operable (a) to allow the flow of the fluid from the reservoir to the cuff in response to the operation of the pumping means, and (b) to allow the flow of the fluid from the cuff to the reservoir, the valving means including a valve element biased against a valve seat and movable between an open position and a closed position; and a drainage passage through the valve seat that remains open when the valve element is in the closed position, the diameter of the drainage passage being calculated to provide a flow rate of the fluid from the cuff to the reservoir when the valve element is in the closed position such that a substantial deflation of the cuff results when a predetermined time interval has elapsed.

10. The device of claim 9, wherein the inflatable cuff is a first inflatable cuff, wherein the device further comprises a second inflatable cuff adapted to receive and engage a surgically-created penile arteriovenous anastamosis, and wherein the cuff actuation means is selectively operable for (a) inflating the second cuff while deflating the first cuff, and (b) deflating the second cuff while inflating the first cuff.

11. The device of claim 9, further comprising: drug delivery means, implantable in the body of the patient, for delivery a predetermined quantity of a liquid to the penile tissue of the patient in response to the flow of fluid from the reservoir to the cuff.

12. A device for treating impotence in a human male patient, comprising:

an inflatable cuff, implantable in the patient so as to receive and engage a penile vein or a crus of a corpus cavernosum of the patient; and cuff actuation means, implantable in the patient, and operable by the patient, for selectively inflating and deflating the cuff, thereby selectively and reversibly restricting the blood flow through the vein or crus, the cuff actuation means comprising:

a fluid-filled squeeze bulb;

conduit means for providing fluid communication between the bulb and the cuff;

valving means for allowing the flow of fluid through the conduit means from the bulb to the cuff in response to the collapsing of the bulb due to the application of external pressure thereto, the valving means including a housing defining a fluid flow path between the bulb and the conduit means, and a valve element in the housing, movable between a first position in which the valve element is closed against a valve seat, thereby closing the fluid flow path, and a second position opening the fluid flow path, the valve element being movable from the first position to the second position in response to the pressure-induced collapsing of the bulb;

manual valve actuation means for selectively opening the valving means to allow the flow of fluid through the conduit means from the cuff to the bulb in response to manual operation of the valve actuation means, whereby the valve element is movable from the first position to the second position in response to the manual operation of the valve actuation means; and a drainage passage through the valve seat that remains open when the valve element is closed against the valve seat, the diameter of the drainage passage being calculated to provide a flow rate of the fluid from the cuff to the bulb that results in the substantial deflation of the cuff when a predetermined time interval has elapsed.

13. The device of claim 12, further comprising: drug delivery means, implantable in the body of the patient, for delivering a predetermined quantity of a liquid to the penile tissue of the patient in response to the flow of fluid through the conduit means from the bulb to the cuff.

14. A device for treating impotence in a human male patient, comprising:

a first inflatable cuff, implantable in the patient so as to receive and engage a penile vein or a crus of a corpus cavernosum of the patient;

a second inflatable cuff, implantable in the patient so as to receive and engage a surgically-created penile arteriovenous anastamosis; and cuff actuation means, implantable in the patient, and selectively operable by the patient for (a) inflating the second cuff while deflating the first cuff, and (b) deflating the second cuff while inflating the first cuff.

15. The device of claim 14, wherein the cuff actuation means comprises:

a squeeze-bulb reservoir adapted to receive and contain a fluid;

conduit means for conducting the fluid between the reservoir and the first and second cuffs; and valving means for selectively directing the fluid (a) from the first cuff into the reservoir and then into the second cuff, and (b) from the second cuff into the reservoir and then into the first cuff, in response to pressure applied to the squeeze-bulb reservoir.

16. The device of claim 15, wherein the squeeze bulb reservoir comprises:

a hollow, flexible shell; and an open-celled elastomeric foam material in the interior of the shell, the foam material having interstices adapted to contain the fluid.

17. The device of claim 15, wherein the conduit means includes first and second tubes communicating between the valving means and the first and second cuffs, respectively, and wherein the valving means comprises:

a housing;

fluid flow directing means in the housing for providing a first fluid outflow path from the reservoir to the first tube, a second fluid outflow path from the reservoir to the second tube, a first fluid backflow path from the first tube to the reservoir, and a second fluid backflow path from the second tube to the reservoir; and a valve element movable between a first position and a second position, whereby, in the first position, the valve element opens the first outflow path and the second backflow path, while closing the second outflow path and the first backflow path, and whereby, in the second position, the valve element opens the second outflow path and the first backflow path, while closing the first outflow path and the second backflow path.

18. A device for treating impotence in a human male patient, comprising:

an inflatable cuff, implantable in the patient so as to receive and engage a penile vein or a crus of a corpus cavernosum of the patient;

drug delivery means, implantable in the body of the patient, for delivering a predetermined quantity of a liquid to the penile tissue of the patient; and cuff actuation means, implantable in the patient, and operable by the patient, for selectively inflating and deflating the cuff, thereby selectively and reversibly restricting the blood flow through the vein or crus, the cuff actuation means comprising:

a fluid-filled squeeze bulb;

conduit means for providing fluid communication between the bulb and the cuff; and valving means for allowing the flow of fluid through the conduit means from the bulb to the cuff in response to the collapsing of the bulb due to the application of external pressure thereto, the valving means including manual valve actuation means for selectively opening the valving means to allow the flow of fluid through the conduit means from the cuff to the bulb in response to the manual operation of the valve actuation means;

wherein the drug delivery means delivers the predetermined quantity of the liquid in response to the flow of fluid through the conduit means from the bulb to the cuff.

19. The device of claim 18, wherein the valving means comprises:

a housing defining a fluid flow path between the bulb and the conduit means; and a valve element in the housing, movable between a first position closing the fluid flow path and a second position opening the fluid flow path, the valve element being movable from the first position to the second position in response either to (a) the pressure-induced collapsing of the bulb, or (b) the manual operation of the valve actuation means.

20. The device of claim 19, wherein the valve element is normally closed against a valve seat by biasing means, and wherein the valve actuation means includes means for manually displacing the valve element from the valve seat.

21. The device of claim 20, wherein the means for manually displacing the valve element includes push-button means, comprising:

means defining a flexible portion of the housing;

a push-button seated in the housing so as to be manually operable, the push-button including a protuberance that is engageable against the flexible portion; and valve element engagement means disposed on the flexible portion so as to be operably engageable against the valve element to displace the valve element from the valve seat in response to the flexing of the flexible portion when the push-button is operated to engage the protuberance against the flexible portion.

22. The device of claim 18, wherein the drug delivery means comprises:

a housing defining a first chamber, a second chamber, and a flow passage between the first and second chambers, the first chamber having an inlet and the second chamber having an outlet;

first means for filling the first and second chambers with the liquid through the inlet;

second means in the second chamber for displacing the liquid from the second chamber and out of the outlet in response to the flow of fluid through the conduit means from the bulb to the cuff;

third means for refilling the second chamber with liquid from the first chamber to replace the liquid displaced by the second means; and a drug delivery conduit communicating between the outlet and the penile tissue to which the liquid is to be delivered.

23. The device of claim 22, wherein the second means comprises:

an inflatable element disposed in the second chamber; and inflation tube means, communicating between the inflatable element and the conduit means, for directing fluid from the conduit means into the inflatable element so as to inflate the inflatable element.

24. The device of claim 22, wherein the third means comprises:
- a check valve disposed in the flow passage so as to permit flow from the first chamber to the second chamber; and
- means for applying a pressure to the liquid in the first chamber to cause the liquid to flow through the check valve.

25. The device of claim 24, wherein the means for applying a pressure includes a spring-biased piston disposed in the housing so as to apply a pressure to the first chamber.

26. A method of treating impotence in a human male patient, comprising the steps of:
- (a) selecting a penile vein of the patient;
- (b) implanting, in the body of the patient, implantable means for allowing the patient selectively to restrict the venous outflow of blood from the selected vein when erectile function is desired, normal venous outflow for the patient being otherwise maintained;
- (c) selecting a penile artery near the selected vein; and
- (d) arterializing a portion of the venous blood flow by surgically creating an anastamosis between the selected vein and the selected artery.

27. The method of claim 26, further comprising the step of:
- (e) implanting, in the body of the patient, implantable means for allowing the patient selectively to (1) divert venous outflow from the selected vein, through the anastamosis, and into the selected artery when erectile function is desired, and (2) maintain venous outflow from the selected vein, while occluding the anastamosis when erectile function is not desired.

28. The method of claim 27, wherein the implantable means comprises:
- a first inflatable cuff adapted to receive and engage the selected vein;
- a second inflatable cuff adapted to receive and engage the selected artery;
- a reservoir adapted to receive and contain a biocompatible working fluid; and
- means for selectively (1) inflating the first cuff with the fluid, while deflating the second cuff, when erectile function is desired, and (2) deflating the first cuff, while inflating the second cuff, when erectile function is not desired.

29. The method of claim 26, further comprising the step of:
- (e) introducing a vasoactive drug into the penile tissue of the patient when the venous outflow is restricted.

* * * * *